United States Patent [19]
Soroca

[11] Patent Number: 5,102,337
[45] Date of Patent: Apr. 7, 1992

[54] PREFABRICATED THERMOPLASTIC CLASP

[76] Inventor: Sol Soroca, 722 Carlisle Rd., Jericho, N.Y. 11753

[21] Appl. No.: 465,312

[22] Filed: Jan. 16, 1990

[51] Int. Cl.$^5$ .............................................. A61C 13/12
[52] U.S. Cl. ...................................................... 433/178
[58] Field of Search .......................................... 433/178

[56] References Cited

U.S. PATENT DOCUMENTS

| | | | |
|---|---|---|---|
| 2,631,373 | 3/1953 | Timm | 433/178 |
| 2,748,480 | 6/1956 | Weissman | 433/178 |
| 2,789,350 | 4/1957 | Fischer | 433/178 X |
| 3,436,825 | 4/1969 | Oddo, Jr. | 433/178 |
| 4,014,094 | 3/1977 | Schumann | 433/178 X |
| 4,571,186 | 2/1986 | Pipko | 433/213 X |
| 4,595,364 | 6/1986 | Kusano et al. | 433/185 |
| 4,634,381 | 1/1987 | Kusano et al. | 433/172 |

Primary Examiner—Robert P. Swiatek
Assistant Examiner—Nicholas D. Lucchesi
Attorney, Agent, or Firm—Burton S. Heiko

[57] ABSTRACT

A prefabricated thermoplastic clasp from whose structure a permanent clasp is formed around teeth anchoring partial removable prosthesis and dentures without the necessity of fashioning metal clasps by the lost wax method or by plastic clasps by injection molding processes. The prefabricated clasps are easily contoured by applying heat to the area which the technician wishes to shape and bend. This allows the clasp to be a one step operation thereby omitting time consuming procedures.

6 Claims, 2 Drawing Sheets

PREFABRICATED THERMOPLASTIC CLASP

BACKGROUND OF THE INVENTION

This invention is concerned with using a prefabricated thermoplastic clasp for the final and permanent formation of removable partial bridges.

With this new invention the process of making partials or repairing them is made simpler and saves time for the patient who needs emergency repairs and the intricate processes for the technician who would ordinarily have to use cumbersome lost wax processes for metal or injection molding for plastics. Applicant has developed a prefabricated thermoplastic clasp which embraces the tooth in lieu of metal. Prefabricated soft plastic forms in the shape of clasps have been made before to be used as dies in the burnout procedure and then case in steel. These plastic forms were not the final product. The present invention becomes the final product with the necessary shaping and bending. Not only does it provides for all the variations of teeth in the human mouth but it provides a form for quick use and storage not presently known. All sizes of teeth are accommodated.

DESCRIPTION OF THE PRIOR ART

Previously, standard procedure used involved, cumbersome, and time and money consuming processes. Whether the clasp fitting to the teeth was metal or plastic, the technician ordinarly had to go through the lost wax procedure or the injection molding process. The clasps used were not the final product.

Previous patents wre Napolitano, Orthodontic Method and Apparatus, U.S. Pat. No. 4,850,865 where wires were mounted on teeth, and Dziki, Extra-Oral Dental Restoration, U.S. Pat. No. 4,854,875, where a molten thermoplastic resin was used in restorative dentistry, and Garay, Tooth-anchored Beneficial Agent Delivery Device, U.S. Pat. No. 4,861,268, where a delivery device was adapted to be semi-permanently affixed to an anchoring tooth, and Holsclaw, Dental Bridge and Method, U.S. Pat. No. 4,877,400, where a dental bridge is constructed between abutment teeth, and Alleluia, Method of Making a Dental Prosthesis, U.S. Pat. No. 4,562,882 where a dental prosthesis is made from a metallic base, and Kipp, Support for a Removeable Dental Prosthesis, U.S. Pat. No. 4,380,436 where a removable prosthesis is made, and Rieger, Dental Prosthesis, U.S. Pat. No. 4,846,718 where a lightweight dental prosthesis is made of a thimble shaped metallic substance, and Harvey, Permanent Dental Prosthesis, U.S Pat. No. Re. 32,972 where a permanent secured prosthesis is made, and Bryan, Method for Thermoset-Thermoplastic Molded Article, U.S. Pat. 4,850,871 where a thermoplastic mold is made, and Breads, Method of Making a Dental Appliance, U.S. Pat. No. 4,798,534 where a method of making a dental appliance is outlined, and Salvo, Dental Bridge, U.S. Pat. No. 4,820,157 where a dental bridge is made, and Tatemoto, Denture Base, U.S. Pat. No. 4,826,435 where a dental base of a thermoplastic flouroelastomer is made, and Shoher, Prefabricated Dental Prosthesis, U.S. Pat. No. 4,826,436 where a prefabricated Dental Prosthesis is made without casting, and Tanaka, Material Packs for Preparing Plate Dentures, U.S. Pat. No. 4,838,789 where a photopolymerizable resin is made.

SUMMARY OF THE INVENTION

A device consisting of a prefabricated thermoplastic clasp which holds, fits and anchors a partrial prosthesis. A clasp which in one form has three tails for small, medium and large size teeth becomes the final product when contoured by the technician who applies heat to the area which is to be bent and shaped. An electric heat apparatus with a small orifice and spatula tip allows precise concentration. The clasps are fabricated in clear or tooth color shades and can be added to existing as well as new partials.

One form of the clasp is about 1.08 inches long tapering in thickness from base to tail from 0.08 inches to 0.05 inches. The width of the clasp at its widest is 0.57 inches. All three tails are facing in the same direction with the first tail coming off the base itself and the other two sized tails coming off the long tapering arm opposite the curve.

However, the number of tails on a clasp does not matter except to make available to the technician the right size clasp for the tooth to which it is to be attached.

It is the principal purpose of this invention to provide a clasp for use with new or old partials which when shaped and fitted becomes the final product without requiring other processes and substances.

Another purpose of this invention is to provide a ready made prefabricated thermoplasctic clasp which embraces the teeth to which it is anchored while holding the partial to which it is fitted in lieu of metal clasps.

Another purpose of this invention is to provide a quick, aesthetic and efficient way to construct partials using a prefabricated clear or tooth shaded thermoplastic clasp requiring only shaping and heating to fit and become the final product.

In the best mode the clasp is shaped from the stone cast poured from an impression which is taken by the dentist. The laboratory technician then contours the clasp or clasps to the anchoring teeth with whatever type clasps are needed, and lutes (affixes) them to the partial. For additions or repairs no tryings on are necessary. For new cases a fitting or trying on may be required. However, the clasps are the final finished product.

DETAILED DESCRIPTION OF THE DRAWINGS

While the invention will be described in terms of the preferred embodiments it will be understood that it is not intended to limit the invention to these embodiments. On the contrary, it is intended to cover all alternative, modifications and equivalents as my be included within the spirit and scope of the invention as defined by the appended claims.

Figure 1A:
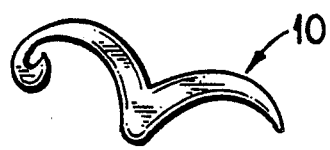
FIGS. 1A through 1G are top plan views of different specialized sizes and shapes of clasps which are used with partial prosthesis.
Figure 2:
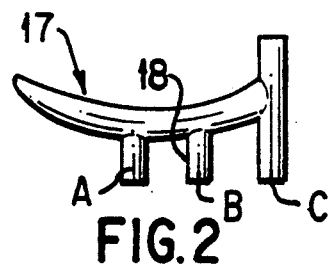
FIG. 2 is a top plan view of the invention showing a clasp presently used with three tails.
Figure 1B:
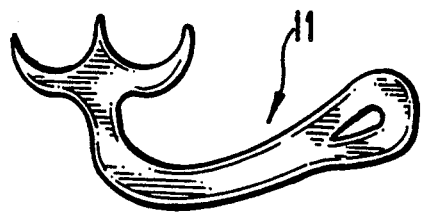

The device is shown in FIG. 2 in its main outline. It consists of a prefabricated thermoplastic device which has three tails spaced accordingly to the size of the tooth being clasped. When this determination is made, the other two tails are removed leaving the contoured clasp and a single tail.

10 through 16 of FIG. 1 are variously shaped clasps that are specialized for use on partial prosthesis. Each of these consists of a clasp which wraps around the crown of the anchoring tooth and a tail which is positioned to engage the partial prosthesis ensuring a snug fit. The tails of the clasp are formed as bars which intersect at an angle with the band portion of the clasp, with the vertex of the angle at the junction of a bar and the elongated band portion of the clasp, as shown in FIG. 2. The bars 18a-18c are coplanar with the band of the clasp.

Figure 2A:
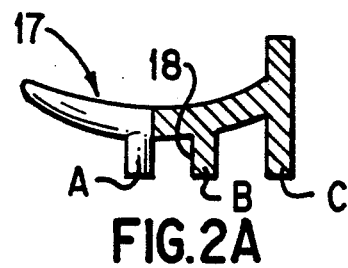
FIG. 2A shows a clasp to fit the smallest tooth with the shaded areas cut off.
Figure 1C:
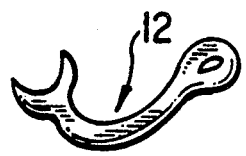
Figure 2B:
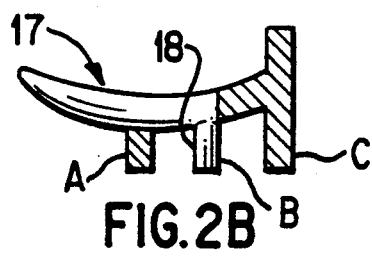
FIG. 2B shows a clasp for a medium size tooth showing the shaded areas cut off.
Figure 1D:

FIG. 2 shows one clasp presently being uses. 17 is the body of the clasp which is wrapped around the crown of the anchoring tooth. The tails are represented by 18 and there are three tails that can possibly be used. As an example the tail closest to the left would be used for a small sized tooth, as shown in FIG. 2A, 18A. The rest of the clasp including the tails, 18B and 18C, would be discarded. A larger tooth, as shown in FIG. 2B, would use the middle tail, 18B, and the other tails, 18A and 18C, would be eliminated and the clasp would wrap around the crown of the anchoring tooth and the tail positioned to lay flat on the ridge area to engage the partial prosthesis.

Figure 2C:
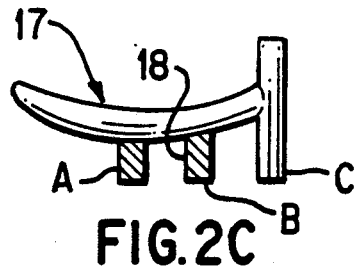
FIG. 2C shows a clasp for a large size tooth with the shaded area cut off.
Figure 1E:
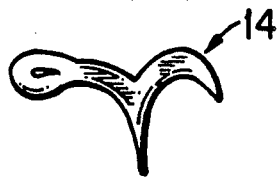

Naturally, larger teeth, as shown in FIG. 2C, would have the last tail, 18C, positioned as the former ones were with the tails, 18A and 18B cut off.

Figure 3:
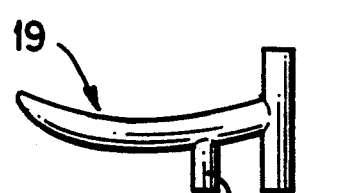
FIG. 3 is a top plan view of a clasp with only 2 tails and FIG. 4 is a view of the clasp shaped around the crown of a tooth showing how the tail is positioned to hold partial prothesis to the clasped tooth.
Figure 1F:
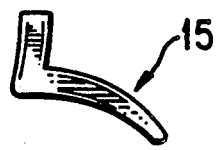
Figure 1G:
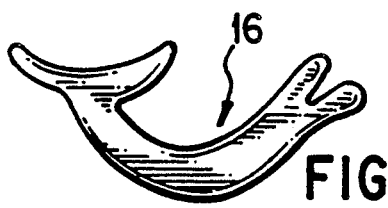

FIG. 3 is to the same effect only using a clasp with 2 possible tails. The clasp, 19, would be wrapped around the holding tooth while either one of the tails would be used depending on the size of the tooth and positioned to engage the partial prosthesis.

Figure 4:
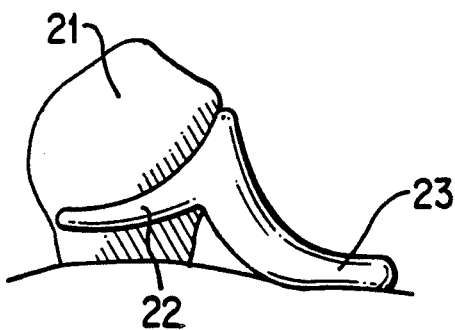

FIG. 4 shows a clasp, 22, wrapped around the crown of the anchoring tooth, 21, with the tail, 23, positioned to be affixed to the partial prosthesis.

Figure 5:
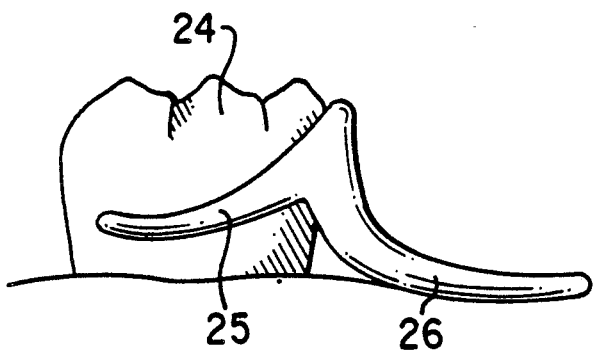
FIG. 5 shows a similar clasp with one side anchored to the molar while the tail is positioned to receive the prosthesis.

FIG. 5 shows a larger molar with its crown, 24, being engaged by the clasp, 25, while its tail is positioned to hold the partial prosthesis.

Figure 6:
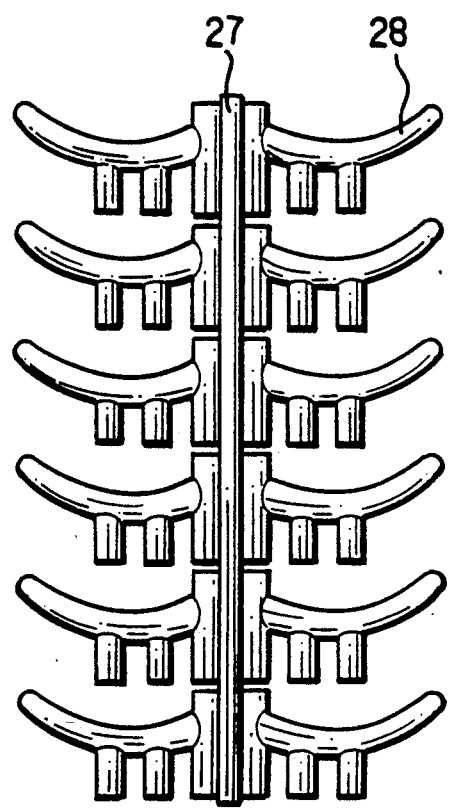
FIG. 6 shows a top plan view revealing how one type of clasp can be positioned on a stem ready for use.
Figure 7:
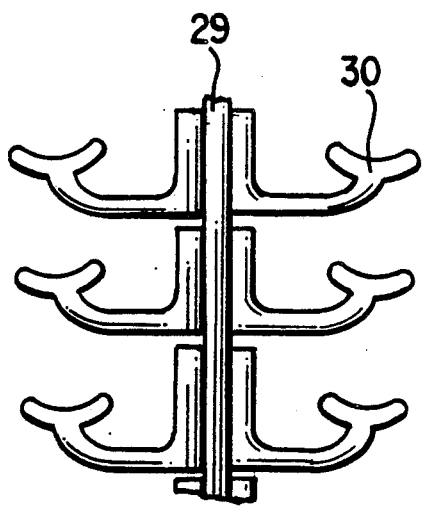
FIG. 7 shows a top plan view of specialized clasp positioned on a stem ready for multiple uses.

FIGS. 6 and 7 show different types of clasps affixed to a tree like stem, 27 and 29 respectively, holding each individual clasp before use, 28 and 30 respectively. Each individual clasp can easily be broken away from the stem and then used, cut, and shaped as desired. This way ready availability in useful form and convenience is at the dental technician's immediate call.

As an example, suppose the requirement is that the first bicuspid, which has a clasp, is being extracted and the clasp is being moved to the cuspid.

Firstly, the dentist has to take an impression of the area where the partial is needed and from this impression the stone model is poured. Then the technicial working from the stone model which is a replica of the mouth proceeds as follows:

a) The metal clasp is cut off and the existing acrylic saddle an area is prepared by making room for the new plastic clasp.

b) Burr out enough of an area for the tail of the clasp to lie against proximal of abutment tooth, but not into an undercut.

c) Measure tooth from mesial to center of distal proximal wall to determine which tail will be appropriate for size of clasp.

d) Trim accordngly.

e) Apply heat in a rotating motion and adapt clasp according to survey.

f) Tack with wax.

g) Spray with a separator like "Paint-N-Pour" (®) and hold in place with plaster leaving tail area exposed.

h) Cut undercuts into tail area.

i) Lute with quick cure acrylic and put in pressure pot (lukewarm water). Remove plaster and define adaptation with heat gun.

j) Finish and polish

The new type of prefabricated thermoplastic clasp which is the basic of this invention becomes the final product once shaped. A clasp is retentive device which engages an abutment tooth. An abutment tooth is the selected tooth to which the clasp is affixed. Basically, thermoplastics are replacing metal clasps. Metal clasps are either wrought wire, which is hand bent to shape, or cast as in the lost wax technique. The prefabricated thermoplastic clasp is preformed with retentive tails at different intervals depending on the size requirements and is the final product. There can be various sizes with different retentive loops and shapes designed to fulfill the same premise. The prefabricated tails are made from thermoplastics that can be easily contoured and tacked to an already existing prosthesis or for starting a new one. The shape and size of the clasps as well as the tails can be different. A heating apparatus with a small orifice for an opening is required to heat and shape the clasp around the stone tooth. When the clasps have been satisfactorily contoured, they are tacked with a quick cure methyl methacrylate and added to the partial. Clasps are then refined, finished and polished and sent back to the dentist.

I claim:

1. A method of using a preformed thermoplastic clasp for holding a partial prosthesis to an anchoring toth, the method comprising:

(a) providing a thermoplastic clasp having an elongated band tapering to a smaller thickness at one end of the clasp, and (b) forming a plurality of parallel bars at the other end of said clasp, and (c) forming an angle between one of said bars, and said band, with the vertex of the angle at the junction of said one of said bars, and said band, said bars and said band lying in the same plane, and (d) fastening said band to a working model of said anchoring tooth by heating and contouring said band thereto, and (e) affixing said clasp to said partial prosthesis with a quick setting acrylic.

2. The method according to claim 11, further comprising curing and finishing the thermoplastic material of the clasp.

3. The method according to claim 1 further comprising arranging and attaching a plurality of clasps to a holding member.

4. In a process for attaching a thermoplastic clasp to an anchoring tooth, and affixing a new or old partial prosthesis to the clasp so that it fits into the mouth, the improvement comprising:

(a) shaping an elongated prefabricated thermoplastic clasp having a tail, to anchor the clasp around a crown of an anchoring tooth, and (b) heating and shaping an elongated part of said clasp around said crown, thus permanently shaping said part, and, (c) affixing said tail of said clasp to a partial prosthesis by tacking with a quick cure adhesive.

5. The process according to claim 4, wherein the improvement further comprises forming said clasp of sufficient size to fit any selected tooth.

6. The process according to claim 4, wherein the improvement further comprises making said clasp tooth or gum colored.

* * * * *